US009567247B2

(12) United States Patent
Josse et al.

(10) Patent No.: US 9,567,247 B2
(45) Date of Patent: *Feb. 14, 2017

(54) SYNGAS BIOMETHANATION PROCESS AND ANAEROBIC DIGESTION SYSTEM

(71) Applicant: Anaergia Inc., Burlington (CA)

(72) Inventors: Juan Carlos Josse, Mission Viejo, CA (US); Andrew Benedek, Rancho Santa Fe, CA (US)

(73) Assignee: Anaergia Inc., Burlington (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/826,507

(22) Filed: Mar. 14, 2013

(65) Prior Publication Data
US 2013/0203144 A1 Aug. 8, 2013

Related U.S. Application Data

(63) Continuation-in-part of application No. PCT/CA2013/050037, filed on Jan. 21, 2013.

(60) Provisional application No. 61/589,663, filed on Jan. 23, 2012, provisional application No. 61/652,260, filed on May 28, 2012.

(51) Int. Cl.
| C12P 5/02 | (2006.01) |
| C02F 3/28 | (2006.01) |
| C02F 3/12 | (2006.01) |
| C02F 11/04 | (2006.01) |
| C02F 11/10 | (2006.01) |
| C10K 1/04 | (2006.01) |
| C10B 53/00 | (2006.01) |
| C10B 53/02 | (2006.01) |
| C05F 11/00 | (2006.01) |
| C02F 11/12 | (2006.01) |

(52) U.S. Cl.
CPC .............. *C02F 3/2893* (2013.01); *C02F 3/12* (2013.01); *C02F 11/04* (2013.01); *C02F 11/10* (2013.01); *C05F 11/00* (2013.01); *C10B 53/00* (2013.01); *C10B 53/02* (2013.01); *C10K 1/04* (2013.01); *C12P 5/023* (2013.01); *C02F 3/28* (2013.01); *C02F 11/12* (2013.01); *C02F 11/121* (2013.01); *C02F 2203/00* (2013.01); *Y02E 50/14* (2013.01); *Y02E 50/343* (2013.01); *Y02P 20/145* (2015.11); *Y02W 10/40* (2015.05); *Y02W 30/47* (2015.05); *Y10T 137/85978* (2015.04)

(58) Field of Classification Search
None
See application file for complete search history.

(56) References Cited

U.S. PATENT DOCUMENTS

| 4,289,625 A * | 9/1981 | Tarman et al. .............. 210/603 |
| 4,880,473 A | 11/1989 | Scott et al. |
| 5,017,196 A * | 5/1991 | Dewitz ........................ 48/210 |
| 5,395,455 A | 3/1995 | Scott et al. |
| 5,417,492 A | 5/1995 | Christian et al. |
| 5,424,417 A | 6/1995 | Torget et al. |
| 5,605,551 A | 2/1997 | Scott et al. |
| 5,865,898 A | 2/1999 | Holtzapple et al. |
| 5,959,167 A | 9/1999 | Shabtai et al. |
| 6,022,419 A | 2/2000 | Torget et al. |
| 6,048,374 A | 4/2000 | Green |
| 6,228,177 B1 | 5/2001 | Torget |
| 7,229,483 B2 | 6/2007 | Lewis |
| 7,494,637 B2 | 2/2009 | Peters et al. |
| 7,578,927 B2 | 8/2009 | Marker et al. |
| 7,608,439 B2 | 10/2009 | McTavish et al. |
| 7,972,824 B2 | 7/2011 | Simpson et al. |
| 8,383,871 B1 | 2/2013 | Sellars et al. |
| 2007/0117195 A1 | 5/2007 | Warner et al. |
| 2007/0217995 A1 | 9/2007 | Matsumura et al. |
| 2008/0236042 A1 | 10/2008 | Summerlin |
| 2008/0280338 A1 | 11/2008 | Hall et al. |
| 2009/0151253 A1 | 6/2009 | Manzer et al. |
| 2009/0229595 A1 | 9/2009 | Schwartz |
| 2009/0239279 A1 | 9/2009 | Hall et al. |
| 2010/0021979 A1 * | 1/2010 | Facey et al. ................. 435/147 |
| 2010/0133085 A1 | 6/2010 | Hutchins et al. |
| 2010/0162627 A1 * | 7/2010 | Clomburg et al. ...... 48/197 FM |
| 2010/0223839 A1 | 9/2010 | Garcia-Perez et al. |
| 2010/0317070 A1 | 12/2010 | Agaskar |
| 2011/0033908 A1 | 2/2011 | Cheong et al. |
| 2011/0179700 A1 | 7/2011 | Monroe et al. |
| 2011/0248218 A1 | 10/2011 | Sutradhar et al. |

(Continued)

FOREIGN PATENT DOCUMENTS

| BR | 009401102 | 11/1994 |
| CA | 2628323 | 6/2007 |

(Continued)

OTHER PUBLICATIONS

Lehmann et al. "Bio-Char Sequestration in Terrestrial Ecosystems—A Review" Mitigation and Adaptation Strategies for Global Change (2006) 11: 403-427.*
Linden et al. "Gaseous Product Distribution in Hydrocarbon Pyrolysis" Industrial and Engineering Chemistry vol. 47, No. 12, pp. 2470-2474.*
Sustarsic "Wastewater Treatment: Understanding the Activated Sludge Process" CEP Nov. 2009, pp. 26-29.*
Guiot, S.R. et al (Mar. 2011), Potential of wastewater-treating anaerobic granules for biomethanation of synthesis gas, Environmental Science and Technology, vol. 45, Issue 5, pp. 2006-2012.
Bredwell, M.D., et al., (1999), Reactor Design Issues for Synthesis-Gas Fermentations, Biotechnology Process, vol. 15, Issue 5, pp. 834-844.
Cozzani et al., A fundamental study on conventional pyrolysis of a refuse-derived fuel, Ind. Eng. Chem. Res. 1995, 34, 2006-2020.
International Search Report of PCT/CA2013/050037.
Lewis, F.M, et al.; A Powerful byproduct, WEFTEC, Jan. 2008, pp. 64-69.

(Continued)

Primary Examiner — Thane Underdahl

(57) ABSTRACT

An anaerobic digester is fed a feedstock, for example sludge from a municipal wastewater treatment plant, and produces a digestate. The digestate is dewatered into a cake. The cake may be dried further, for example in a thermal drier. The cake is treated in a pyrolysis system to produce a synthesis gas and biochar. The gas is sent to the same or another digester to increase its methane production. The char may be used as a soil enhancer.

8 Claims, 1 Drawing Sheet

(56) References Cited

U.S. PATENT DOCUMENTS

| | | |
|---|---|---|
| 2012/0073199 A1 | 3/2012 | Lewis |
| 2012/0322130 A1 | 12/2012 | Garcia-Perez et al. |

FOREIGN PATENT DOCUMENTS

| | | | |
|---|---|---|---|
| CA | 2641270 | 12/2009 | |
| DE | 10107712 A1 | 9/2002 | |
| JP | 2003-089793 | 3/2003 | |
| WO | 0179123 A1 | 10/2001 | |
| WO | 2004060587 | 7/2004 | |
| WO | WO 2004/060587 * | 7/2004 | ............ B09B 3/00 |
| WO | 2010001137 | 1/2010 | |
| WO | 2012166771 | 12/2012 | |
| WO | 2012166771 A3 | 12/2012 | |
| WO | 2013110186 | 8/2013 | |

OTHER PUBLICATIONS

Yang, Bin et al.; Pretreatment: the key to unlocking low-cost cellulosic ethanol, Biofuels, Bioprod. Bioref. 2:26-40 (2008).

Liaw, Shi-Shen et al.; Effect of pyrolysis temperature on the yield and properties of bio-oils obtained from the auger pyrolysis of douglas fir wood, Journal of Analytical and Applied Pyrolysis, vol. 93, Jan. 2012, pp. 52-62.

Shanley Pump and Equipment, Inc., EDUR Pumps, http://www.shanleypump.com/edur_pumps.html, printed May 30, 2014.

Jenkins, Scott; Oxidation-based water-reuse technology that improves mass transfer, Chemical Engineering, Feb. 2013, p. 12.

Mahulkar, A.V. et al; Steam Bubble Cativation, AIChE Journal, vol. 54, Issue 7, pp. 1711-1724, Jul. 2008.

Smith, Matthew et al., Integrating Pyrolysis and Anaerobic Digestion, The Northwest Bio-energy Symposium, Nov. 13, 2012, Seattle, Washington, 44 pgs.

Laemsak, Nikhom, Wood Vinegar presentation, Undated, 5 pages.

Jones, S. B. et al.: 'Production of Gasoline and Diesel from biomass via Fast Pyrolysis' Hydrotreating and Hydrocracking: A Design Case, U.S. Department of Energy, PNNL-18284 Feb. 28, 2009, 76 pages.

Laird, David A. et al., Sustainable Alternative Fuel Feedstock Opportunities, Challenges and Roadmaps for Six U.S. Regions; Chapter 16: Pyrolysis and Biochar—Opportunities for Distributed Production and Soil Quality Enhancement, Proceedings of the Sustainable Feedstocks for Advance Biofuels Workshop, Atlanta, GA, Sep. 28-30, 2010 pp. 257-281.

Garcia-Perez, Manuel; Challenges and Opportunities of Biomass Pyrolysis to Produce Second Generation Bio-fuels and Chemicals, Auburn University, Jun. 13, 2012, 66 pages.

Parry, Dave; Biosolids Technology Advances, Jan. 2012, 20 pages.

Melin, K. et al. Evaluation of lignocellulosic biomass upgrading routes to fuels and chemicals, Cellulose Chemistry and Technology 44 (4-6), 117-137 (2010).

Gullu, Dogan et al. Biomass to methanol via pyrolysis process, Energy Conversion and Management, vol. 42, Issue 11, Jul. 2001, pp. 1349-1356.

Demirbas, Ayhan, Biomass resource facilities and biomass conversion processing for fuels and chemicals, Energy Conversion and Management, vol. 42, Issue 11, Jul. 2001, pp. 1357-1378.

Demirbas, Ayhan, The influence of temperature on the yields of compounds existing in bio-oils obtained from biomass samples via pyrolysis, Fuel Processing Technology 88 (2007) 591-597.

AWWTA, Standard Methods, Section 2540G, (2000).

ASTM, Section D3172, Proximate Analysis of Coal and Coke, (2007).

Parry, D.L. et al. "Prolysis of Dried Biosolids for Increased Biogas Production" Proceedings of the Water Environment Federation, Residuals and Biosolids (Mar. 2012), pp. 1128-1139.

Lian, Jieni et al., Separation, hydrolysis and fermentation of pyrolytic sugars to produce ethanol and lipids, Bioresource Technology V. 101 (Dec. 2010), pp. 9688-9699.

* cited by examiner

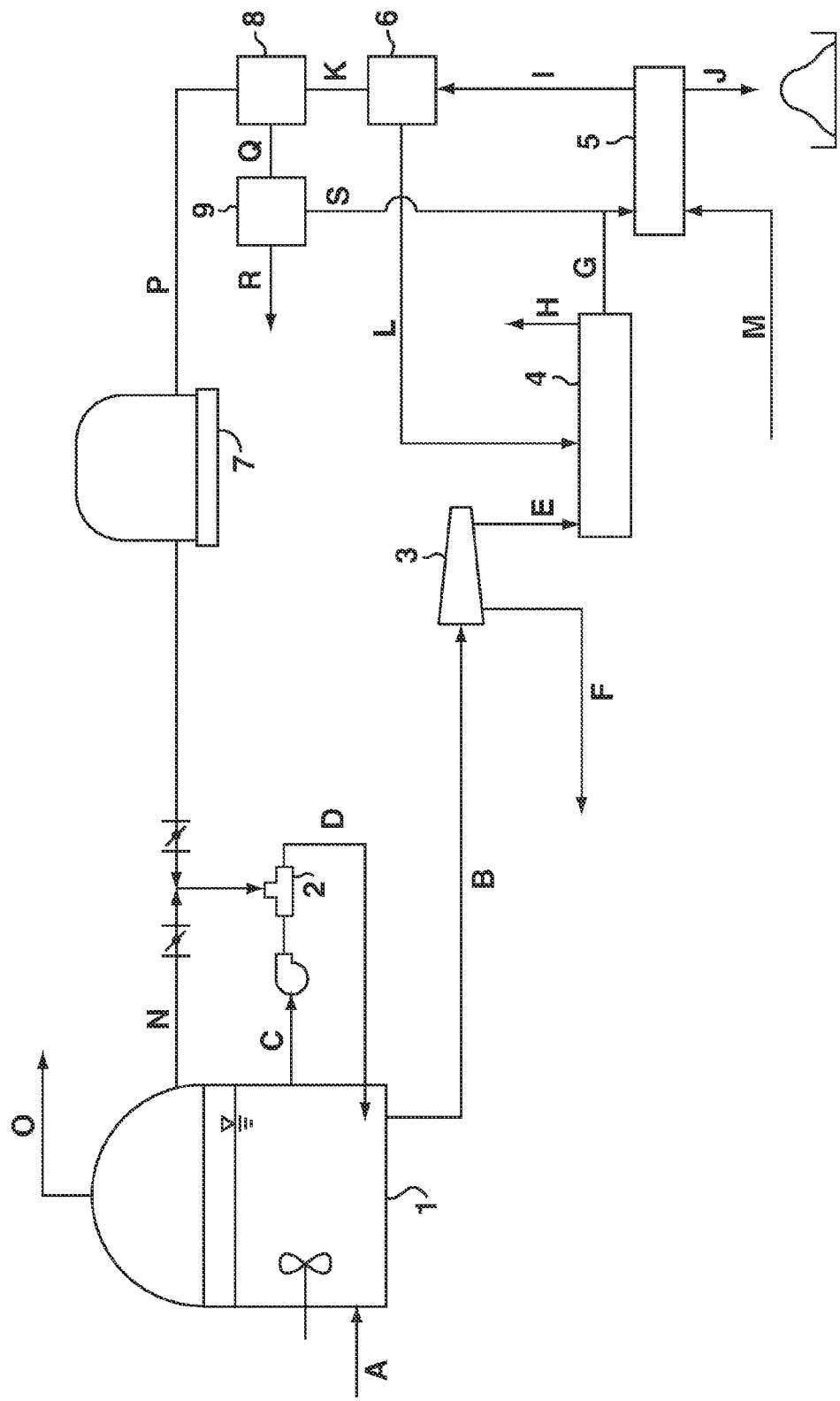

SYNGAS BIOMETHANATION PROCESS AND ANAEROBIC DIGESTION SYSTEM

CROSS-REFERENCES TO RELATED APPLICATIONS

This application is a continuation-in-part of PCT/CA2013/050037 filed on Jan. 21, 2013, which claims the benefit of priority from U.S. Provisional Application Nos. 61/589,663 filed on Jan. 23, 2012 and 61/652,260 filed on May 28, 2012. PCT/CA2013/050037 filed on Jan. 21, 2013 and U.S. Provisional Application Nos. 61/589,663 filed on Jan. 23, 2012 and 61/652,260 filed on May 28, 2012 are incorporated by reference.

FIELD

This specification relates to wastewater treatment, anaerobic digestion, pyrolysis and gasification.

BACKGROUND

The following discussion is not an admission that anything discussed below is common general knowledge or citable as prior art.

Anaerobic digestion produces biogas as a result of the biological fermentation of volatile solids (VS) supplied with the feedstock. The degree of volatile solids reduction is related to the biodegradability of the feedstock and process conditions in the digester. Important digester parameters or considerations include temperature, pH, food-to-microorganism ratio, organic loading rate, hydraulic and solids retention time, absence of toxic substances at inhibitory concentrations, adequate mixing, and others. The closer these conditions are to an optimum, the higher the VS reduction will be.

Typically, digesters treating complex organic substrates will achieve 60 to 80% VS reduction. With substrates with high fiber content, such as silage or dairy manure, a digester may achieve about 60% VS destruction. Typical digesters treating municipal sewage sludge produced in a wastewater treatment plant usually achieve about 50% VS destruction in 20 day hydraulic retention time (HRT) mesophilic digesters.

The digester sludge, or digestate, produced by an anaerobic digester is a combination of inert solids that were fed with the substrate, recalcitrant volatile solids that could not be degraded biologically, and bacterial biomass that grew as a result of feeding on the degradable portion of the volatile solids fed with the feedstock. A typical digestate solids content is 2% to 10% total solids (TS) or dried solids (DS), depending on the substrate and the type of digester. The digestate may be dewatered mechanically to produce a cake with 20 to 30% solids, depending among other things on the undigested fiber content and the type of dewatering device used.

Pyrolysis is a technique typically used to process solid waste such as wood chips or sawdust. Pyrolysis produces biochar, liquids and gases from a biomass by heating the biomass in a low or no oxygen environment. The absence or deficiency of oxygen prevents combustion. The relative yield of products from pyrolysis varies with temperature. Temperatures of 400-500° C. (752-932° F.) produce more char, while higher temperatures, up to and above 700° C. (1,292° F.) favor the yield of liquid and gas fuel components. Pyrolysis occurs more quickly at the higher temperatures, typically requiring seconds instead of hours. High temperature pyrolysis is also known as gasification, and produces primarily synthesis gas. Once initiated, both processes can be self supporting and produce net energy, not accounting for the energy value of the biomass consumed.

Synthesis gas, also called syngas or producer gas, is a combination of CO, $H_2$ and $CO_2$ that results from the thermal degradation of biomass without combustion, through pyrolysis or gasification. This process occurs typically at temperatures between 500 and 700 deg C. with minimal introduction of oxygen, if any. Other components of syngas are water vapor, methane, light hydrocarbons, particulates and volatile impurities. Syngas has a low heat value, for example 120 to 150 Btu/cubic foot. After adequate cleaning to remove moisture, particulates, tars and impurities, syngas can be used for heat or electricity production with adapted internal combustion engines, boilers, gas turbines, or fuel cells. In some gasification systems, syngas is subject to high temperature steam reformation to produce hydrogen that is either sold as a gaseous fuel or used on site to power fuel cells.

In some cases, syngas is upgraded to methane with chemical catalysts. In one process, a water-gas shift (WGS) step increases the $H_2$/CO ratio of the syngas and is followed by a nickel catalyst supported step that enables conversion from CO and $CO_2$ into methane and water. This process is costly due to the chemical catalyst, its energy demand, and the need to pre-treat the syngas to remove impurities.

INTRODUCTION TO THE INVENTION

The following introduction is intended to introduce the reader to the detailed description and claims to follow, but is not intended to limit or define the claims.

The solids in digestate have an energy content resulting from their potential to be oxidized. This energy content can be extracted by pyrolysis or gasification of the digestate to produce syngas, optionally after further drying or dewatering. The syngas can be converted to a biogas containing mostly methane by anaerobic microorganisms.

In a process and apparatus described herein, syngas is added into an anaerobic digester to produce methane. The syngas can come from pyrolysis or gasification of a raw biomass such as wood, municipal solids waste, municipal yard waste, waste activated sludge from municipal sewage treatment, agricultural residues, etc., or from pyrolysis or gasification of a dewatered and optionally partially dried digestate cake produced by the same or another digester at the same or another digestion facility. For example, the digester may be part of a municipal wastewater treatment plant or an agricultural or industrial digester. Methane production in the digester increases. The syngas may be added to the digester without pretreatment other than lowering its temperature.

An apparatus and process are described herein for transferring syngas to digestate. A jet ejector pump is used to aspirate into a stream of digestate flowing in a pipe. The digestate may be flowing in a dedicated recirculation loop. A pump generates a primary flow. An ejector nozzle at the pump discharge draws and mixes a secondary flow of syngas into the primary flow. The liquid and gas are combined into a liquid jet containing fine syngas bubbles. This mixture exits in one or more locations in a digester tank.

Optionally, the pumped jet aspiration system may also provide mixing for the digester. In another option, gas from the headspace of the digester can be mixed into digestate to encourage further conversion of CO and $H_2$ in the syngas or biogas to methane. In another option, heat from syngas leaving a pyrolysis reactor may be recovered and used, for example, for partial drying of the digestate.

Optionally, a condensable portion of the syngas may be condensed, for example by indirect condensing, and fed to the digester as a liquid. A remaining gas portion of the syngas is fed to the digester as described above.

In a process and apparatus for treating wastewater, such as municipal sewage, a digestate cake is further thermally dried and then fed to a pyrolysis system to produce syngas and char. The syngas is preferably cooled to recover its heat for cake drying, and then introduced into one or more anaerobic digesters for bioconversion of syngas into methane. The methane may be used as a fuel for heat or generating electricity. The biochar resulting from the pyrolysis process may be used as soil enhancer.

BRIEF DESCRIPTION OF THE FIGURES

FIG. 1 is a schematic process flow diagram of an anaerobic digestion and pyrolysis system.

DETAILED DESCRIPTION

In this specification, the term pyrolysis includes pyrolysis, gasification, and related methods involving heating biomass without sufficient oxygen to support combustion. The term syngas includes, unless stated otherwise, vapors such as vaporized pyrolysis oil, water vapor, and vapors of pyroligneous acid. The word digestate is sometimes used to refer to only the solids fraction of the sludge produced by an anaerobic digester but in this specification digestate typically refers to the whole digester sludge.

There is experimental evidence that syngas can be converted through anaerobic digestion to biogas containing mainly methane. CO in the syngas is used as a substrate or food for certain strains of methanogenic archea in direct reactions that include hydrogen and water to produce methane. Other indirect reactions also occur, wherein CO and $H_2$ are converted to acetate or methanol and finally to methane by anaerobic bacteria. Regardless of the specific reaction, the methane yield is 0.25 mol of $CH_4$ per mol of CO, plus 0.25 mol of $CH_4$ per mol of $H_2$. Based on the range of CO and $H_2$ typically contained in syngas, this is equivalent to about 0.2 to 0.4 standard $m^3$ of methane production per kilogram of VS gasified, when the syngas is efficiently introduced and dissolved in the anaerobic mixed liquor. The range in syngas composition is a function of the type of biomass gasified and the conditions of the pyrolysis process.

The solids in dewatered digestate cake have a lower energy content than the undigested raw solids in the digester feedstock because a portion of the carbon contained in the VS was converted by digester anaerobic bacteria into methane and carbon dioxide. In the case where a combination of primary and secondary municipal sewage sludge (for example from an activated sludge sewage plant) is fed to a digester, the energy content of undigested solids with a 70% VS content may be about 7000 Btu per pound of dry solids (DS). In anaerobic digester sludge with a 48% VS content, the energy value may be 4800 Btu/lb DS depending on the degree of VS reduction. Depending on the VS content of the raw municipal sewage sludge, its heat content can be as high as 7400 Btu/lb DS, and the heat content of the anaerobic digester sludge may be as high as 5700 Btu/lb DS. The digestate produced from feedstocks with higher fiber content tends to have a higher heat value.

The energy value of the digestate solids can be extracted by pyrolysis or oxidation of the dewatered cake. Depending on the heat content of the digestate solids, further thermal drying after mechanical dewatering may be required to be able to support auto-thermal pyrolysis of the digestate to produce syngas without the need to introduce additional external heat to support pyrolysis. The solids content required to support auto-thermal pyrolysis may range from 40% to 70% or higher. Depending on the type of pyrolysis equipment, required solids content of the feed may be as high as 90%.

The cake can be dried using direct or indirect dryers. Direct belt dryers are more versatile as they enable the use of low temperature heat sources such as heat recovered from engine generators, condensate, etc.

The syngas is introduced into a digester for the purpose of producing methane. The syngas can come from one or more of any form of gasified raw biomass such as wood, municipal solids waste, municipal yard waste (for example grass clippings, leaves or plant clippings), primary or waste activated sludge from a wastewater treatment plant such as a municipal sewage plant, agricultural residues, etc.; or from pyrolysis/gasification of dewatered and partially dried digestate cake produced by the same or other digester at the same or other digestion facility. The facility can be a municipal wastewater treatment plant or an agricultural or industrial digester. Methane production in the digester increases as it results from two sources, the fermentation of VS in the feedstock and the bioconversion of the syngas (CO and $H_2$) to methane. Syngas does not require pretreatment for introduction into the digester, only lowering its temperature. In cases where the pyrolysis feedstock includes lignocellulosic material, pyrolysis allows carbon in the lignocellulosic material to be consumed in the digester.

The solubility of CO and $H_2$ in water is low, therefore syngas biological conversion to methane is limited by the gas-liquid mass transfer. To increase the gas liquid mass transfer rate, the syngas is preferably added to the digestate in small bubbles, for example of 1000 microns or less in diameter, or by transfer across a gas permeable membrane.

A jet ejector pump or aspirator may be used to aspirate syngas. The syngas may be cooled and stored in a gas holder. A pump recirculates sludge from the digester. This pump can be, for example, a chopper pump or an open impeller end suction centrifugal pump. The pump generates a primary flow. An ejector nozzle at the pump discharge reduces the pipe diameter and accelerates the sludge flow, lowering the pressure. This results in a secondary flow of syngas from the gas holder being drawn into the ejector. The turbulence in the ejector nozzle causes an active mixing zone where the liquid and gas are combined into a liquid jet containing fine syngas bubbles. The mixture exits in one or more locations around the lower third of the digester tank where jet nozzles are placed. This increases the mass transfer between gas and liquid and enables the syngas to dissolve in the digestate. Further, if the gas includes vapors, contact with the liquid condenses the vapors while heating the liquid.

An alternative method to create syngas microbubbles is to use a microbubble generator pump, such as made by Honda Pumps. These pumps are used for dissolved air flotation or ozone injection and create gas microbubbles of 50 micron diameter or less, which may be an order of magnitude smaller than bubbles produced by many gas eductors or aspirators. The microbubbles are dispersed in recirculating digestate or filtrate flow by connecting the pump gas inlet to the syngas storage holder. With smaller bubbles, the gas/water interface surface area is increased, gas holdup time in the water column also increases, and digester foaming is reduced.

The syngas may include one or more condensable gasses. In that cases, the condensable gasses may be introduced into the digester as a gas as described above. Alternatively, at least some of the condensable gas may be condensed and introduced into the digester as a liquid. For example, the syngas may go through an indirect condensing step before remaining gas is fed to the digester.

In digesters with high solids content and fibers in the digestate, a screw press or other solids separator can be used to produce a filtrate that is more suitable for receiving syngas bubbles. The recirculating digestate or filtrate stream is used primarily for gas/liquid mass transfer but may also serve the purpose of total or partial mixing, particularly in digesters operated with low solids content (2 to 4%). In digesters with higher solids content further mechanical mixing is likely to be required. However, mixing may bring syngas bubbles to the surface of the digester before they have a chance to dissolve into the digestate. Many digesters are mixed intermittently, for example ¼ to ⅓ of the time. Optionally, microbubbles or larger ejector or aspirator gas bubbles may be fed only during non-mixing periods to reduce short-circuiting of bubbles to the surface aided by vertical mechanical mixing energy.

When implemented in a high solids digester such as a two stage Triton™ digester from UTS or Anaergia, sludge from the second stage may be used for recirculation and gas entrainment, as the solids content is lower and so is the viscosity. Syngas reintroduction is preferably done in the second stage of high solids two stage digesters. The syngas injection process can be used with mesophilic or thermophilic digesters, but the conversion efficiency of syngas to methane is higher under thermophilic conditions.

An intake to the aspirator nozzle can also be connected to the headspace of the digester, such that the nozzle aspirates a combination of biogas and syngas. The relative flow of the gasses is regulated with valves in one or both gas supply lines. If the quality of the biogas collected in the headspace of the digester decreases (increased CO and $H_2$ content) materially as a result off syngas introduction into the digester liquid, this is an indication of incomplete syngas conversion to methane. Biogas from the headspace can be reintroduced into the digester liquid so that CO and $H_2$ in the headspace gas are converted to methane.

Syngas will exit the pyrolysis reactor at 250 degrees C. or more, or 400 or 500 to 700 deg C. or more. The syngas is cooled for introduction into the digester. A gas/liquid heat exchanger can be used to recover heat from the syngas. The heat recovered as hot water can be used for partial drying of the cake in a low temperature direct belt dryer. Another option to recover heat from the syngas for cake drying is to use a gas/gas heat exchanger wherein syngas heat is transferred to air used in the belt dryer.

Preferably, the temperature and residence time of the pyrolysis reactor are sufficient to produce syngas wherein components other than water vapor are primarily carbon monoxide or hydrogen. However, there may also be other condensable gasses or liquid droplets in the syngas of other compounds such as oils, waxes or other organics, collectively called "oils" or "organics". A syngas condenser, downsteam of or integrated with the gas heat exchanger, condenses the syngas to allow the water vapor and oils to be removed as a liquid fraction of the syngas from a gas fraction of the syngas. The syngas condenser may be, for example, a direct condenser having a recirculated cooled syngas liquid fraction within a contact chamber or an indirect condenser.

The gas fraction of the syngas flows to a gas holder and eventually to the anaerobic digester. The liquid fraction of the syngas optionally flows to an oil-water separator, for example a centrifuge, to create a water fraction and an organics fraction. The water fraction may be discharged for further treatment, optionally to the anaerobic digester if discharge to a sewer is not permitted and no other treatment means are located nearby. The water fraction contains some residual organics and so operates as a bleed preventing the accumulation of recalcitrant compounds.

The organics fraction of the liquid fraction of the syngas may be sent to the digester but it is preferably returned to the pyrolysis reactor. In the pyrolysis reactor, at least a portion of the returned organics are converted to carbon monoxide and hydrogen or other gaseous components of the syngas. This effectively increases the residence time for compounds requiring additional time to be converted into gasses.

Digested sludge disposal in municipal wastewater treatment plants is a growing concern due to rising costs and limitations in the ability to apply the sludge to land. The pyrolysis process results in syngas and char. Char, also called bio-char, contains carbon and ash. Ash is the non-volatile or inert, solids present in the sludge. Some of these solids are nutrients such as phosphorous and potassium or other minerals. Char is a sanitized product as a result of the high temperature process that produces it. The char volume is a fraction of that of the sludge cake, and can be used as soil enhancer. Biochar can be used for one or more purposes such as a soil amendment to improve crop yield, to support crops that require high potash and elevated pH, to improve water quality, to reduce soil emissions of greenhouse gases, to reduce nutrient leaching, to reduce soil acidity, and to reduce irrigation and fertilizer requirements. These positive qualities are dependent on the properties of the biochar, and may depend on regional conditions including soil type, soil conditions, temperature, and humidity. In some cases, modest additions of biochar to soil may reduce nitrous oxide ($N_2O$) emissions by up to 80% and essentially eliminate methane emissions. $N_2O$ and methane are both more potent greenhouse gases than $CO_2$. Biochar can store greenhouse gases in the ground thus potentially helping to reduce or stall the growth in atmospheric greenhouse gas levels. Biochar can sequester carbon in the soil for hundreds to thousands of years, like coal.

In one application, a municipal wastewater treatment plant or process such as an activated sludge plant is coupled with an anaerobic digester. Primary and waste activated (secondary) sludge from the wastewater treatment plant is sent to the digester. The digester produces digestate which is de-watered to produce a cake. The digester sludge cake is further thermally dried and then fed to a pyrolysis system to produce syngas and char. The syngas is cooled, preferably while recovering its heat for example for cake drying. The cooled syngas is introduced into one or more digesters, for example the digester that produced the digestate, for bioconversion of syngas CO and $H_2$ into methane, mediated by bacteria and archea present in the digester bacterial consortium that also ferments the volatile solids fed to the digester in the raw primary and secondary sludge. Optionally, primary and secondary sludge may be fed first to the pyrolysis system rather than being fed to the digester directly. The methane produced by the two processes in the digester combine in the digester headspace and may be used for energy generation with engines, turbines or fuel cells, or upgraded to biomethane for injection into the natural gas grid. The biochar resulting from the pyrolysis process may be used as soil enhancer. Compared to a system in which a digester merely treated sludge from the wastewater treatment plant, there may be less waste produced or the net energy consumption may be reduced, or both, per unit of sewage treated.

Bio-char from gasification of digested municipal sludge or a digestate from an agricultural or industrial digesters can be used as a soil enhancer or a source of nutrients, mainly phosphorous and potassium.

In an example shown in FIG. 1, an anaerobic digester 1, alternatively referred to as a digester for brevity, is combined with a system for pyrolysing its digestate B. The digester 1 is fed with a feedstock A which may comprise one or more of: a sludge, for example primary or waste activated sludge or both from a wastewater treatment plant such as a municipal sewage plant; municipal solid waste; municipal yard waste; an industrial waste; or, an agricultural waste. The digester 1 produces product biogas O which may, for example, be used to produce energy or upgraded to produce biomethane.

The digester 1 may have one or more mixed covered tanks. Suitable digesters are sold under the Triton™ and Helios™ trade marks by UTS or Anaergia. Digestate B flows from the digester 1 to a mechanical dewatering unit 3, for example a centrifuge, filter press or screw press. The mechanical dewatering unit 3 separates the digestate B into a liquid fraction F and a de-watered digestate cake E. The liquid portion F of the digestate B, in some cases called a filtrate or centrate, may be discharged or re-used, optionally after further treatment. Optionally, the digester 1 may be located near a municipal sewage treatment plant and the liquid portion F may be returned to the municipal sewage treatment plant for further treatment. In this case, the digester preferably treats primary and waste activated (secondary) sludge from the sewage treatment plant either as some or all of the digester feedstock A or as some or all of an optional external biomass for gasification M.

The de-watered digestate cake E is sent to an optional sludge cake dryer 4 if required, or beneficial, to reduce the water content of the cake E before pyrolysis. Hot air and moisture H produced by the dryer 4 may be sent to a heat recovery treatment unit to extract waste heat for reuse, for example to help heat the digester 1, the pyrolysis reactor 5 or the dryer 4. The hot air and moisture H may also be treated, for example to reduce ordors, before it is discharged.

The sludge cake dryer 4 produces a partially dried cake G. Some or all of the partially dried cake G which is sent to a pyrolysis reactor 5. Optionally, the pyrolysis reactor 5 may be fed with external biomass M for pyrolysis. The external biomass M may be any one or more of the materials described for the digester feedstock 1. However, the external biomass M is treated by pyrolysis before it enters the digester 1.

The pyrolysis reactor heats its one or more feed materials, for example to between 400 or 500 and 700 degrees C., or alternatively between 175 and 400 degrees C., in the absence or a deficiency of oxygen, to produce biochar J and hot syngas I. Optionally, biochar J may be used as a soil enhancer typically after being collected and stored temporarily and then hauled off site. Hot syngas I is preferably sent to a gas heat exchanger 6 to produce a cooled syngas K and recovered heat L. Recovered heat L may be re-used in the system or elsewhere. For example, recovered heat L may be used to help heat the digester 1, the pyrolysis reactor 5 or the sludge dryer 4.

Cooled syngas K is optionally sent to a syngas condenser 8. The syngas condenser 8 separates the cooled syngas K into a gas fraction P and a liquid fraction Q. The syngas condenser 8 does not necessarily condense all condensable gasses in the cooled syngas K. The liquid fraction Q may be sent to the digester 1. However, the liquid fraction Q is preferably sent to an oil-water separator 9 to produce a water fraction R and an organic fraction S. The water fraction R may contain some organic compounds and may be treated further before it is discharged or-used. The organic fraction S may include water but contains a higher concentration of organic compounds than the liquid fraction Q. The organic fraction S may be treated or upgraded to produce usable products. Alternatively, the organic fraction S is returned to the pyrolysis reactor 5. In this alternative, in the absence of a practical or economical way to make a higher value use of the organic fraction S, the amount of gas fraction P sent to the digester 1 can be increased, which is typically preferable to sending the organic fraction S, or condensable or condensed gases, to the digester 1.

Optionally, the gas fraction P may be collected and stored in a gas holder 7. The gas fraction P may also optionally be mixed with digester biogas N. With or without digester biogas N, the gas fraction P is sent to a pumped gas aspirator 2. Optionally, the gas aspirator 2 may be replaced by another microbubble generator or a gas transfer membrane. recirculating digestate C is withdrawn from the digester 1, typically by way of a pump, and passes through the aspirator 2. Digestate with blended syngas D returns to the digester 1. In this way, the gas fraction P is added to digestate in the digester 1.

Other alternative systems and methods may be devised within the scope of the following claims.

The components and streams in FIG. 1 are listed below, in some cases with additional description.

1. Anaerobic digester
2. Pumped gas aspirator
3. Mechanical dewatering unit
4. Sludge cake dryer
5. Pyrolysis reactor
6. Gas heat exchanger
7. Gas holder (for cooled syngas)
8. Syngas condenser
9. Oil-water separator
A. Digester feedstock
B. Digestate (to dewatering)
C. Recirculating digestate
D. Digestate with blended syngas
E. Dewatered digestate cake
F. Liquid portion (ie. filtrate or centrate) from dewatering, optionally sent to plant headworks or further treatment
G. Partially dried cake (to pyrolysis reactor)
H. Hot air and moisture from dryer, optionally to heat recovery or treatment or both
I. Hot syngas
J. Biochar, optionally to storage or hauling for use as soil enhancer
K. Cooled syngas
L. Recovered heat (from syngas, optionally to cake dryer)
M. External biomass (for pyrolysis)
N. Digester biogas, returning for injection into digester liquid
O. Product biogas, optionally to utilization for energy production or upgrading to biomethane
P. Gas fraction (of syngas)
Q. Liquid fraction (of syngas)
R. Water fraction (of liquid fraction of syngas)
S. Organic fraction (of liquid fraction of syngas)

We claim:

1. A process comprising steps of,
   a) producing a synthesis gas from pyrolysis of a feedstock;
   b) producing a mixture of gasses in the headspace of an anaerobic digester;
   c) withdrawing a portion of the mixture of gasses from the headspace of the anaerobic digester;
   d) withdrawing a stream of digestate from the anaerobic digester;
   e) mixing the withdrawn portion of the mixture of gasses and the synthesis gas into the stream of digestate to produce a stream of digestate comprising the withdrawn portion of the mixture of gasses and the synthesis gas; and
   f) returning the stream of digestate comprising the withdrawn portion of the mixture of gasses and the synthesis gas to the anaerobic digester.

2. The process of claim 1 wherein the feedstock comprises one or more of a raw biomass, wood, municipal yard waste, municipal solids waste, primary sludge from a wastewater treatment plant, waste activated sludge from a wastewater treatment plant or an agricultural waste or residue.

3. The process of claim 1 wherein the feedstock comprises dewatered digestate.

4. The process of claim 3 wherein the dewatered digestate is produced from the digestate withdrawn from the anaerobic digester.

5. The process of claim 1 wherein the anaerobic digester is coupled with or part of a municipal wastewater treatment plant, or an agricultural or industrial digester.

6. The process of claim 1 wherein the synthesis gas is cooled before it is mixed with the digestate.

7. The process of claim 1 wherein condensable organic compounds are removed from the synthesis gas and returned as feedstock to step a).

8. The process of claim 1 wherein the mixing in step e) comprises aspirating the withdrawn portion of the mixture of gasses into the digestate by an ejector.

* * * * *